(12) United States Patent
Greene

(10) Patent No.: US 7,651,615 B2
(45) Date of Patent: Jan. 26, 2010

(54) PROCESS FOR REDUCING WASTE VOLUME

(75) Inventor: Annel Kay Greene, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 0 days.

(21) Appl. No.: 11/645,213

(22) Filed: Dec. 22, 2006

(65) Prior Publication Data

US 2007/0163956 A1 Jul. 19, 2007

Related U.S. Application Data

(60) Provisional application No. 60/753,509, filed on Dec. 23, 2005.

(51) Int. Cl.
*C02F 3/00* (2006.01)
(52) U.S. Cl. ............... 210/620; 210/626; 210/627; 210/760
(58) Field of Classification Search .......... 210/760, 210/620, 626, 627
See application file for complete search history.

(56) References Cited

U.S. PATENT DOCUMENTS

| 2,178,818 | A | 11/1939 | Earp-Thomas |
| 2,209,613 | A | 7/1940 | Roeder |
| RE22,444 | E | 2/1944 | Shook |
| 2,477,815 | A | 8/1949 | Mallory |
| 3,232,434 | A | 2/1966 | Albersmeyer |
| 3,459,303 | A | 8/1969 | Bradley |
| 3,485,750 | A | 12/1969 | Albertson |
| 3,577,341 | A | 5/1971 | Keith, Jr. et al. |
| 3,591,491 | A | 7/1971 | Smith et al. |
| 3,607,737 | A | 9/1971 | Gamer |
| 3,617,537 | A | 11/1971 | Vermette |
| 3,638,793 | A | 2/1972 | Peck |
| 3,660,277 | A | 5/1972 | McWhirter et al. |
| 3,709,364 | A | 1/1973 | Savage |
| 3,803,029 | A | 4/1974 | Blecharczyk |
| 3,806,448 | A | 4/1974 | Smith et al. |
| 3,825,494 | A | 7/1974 | Call et al. |
| 3,838,199 | A | 9/1974 | Coe et al. |
| 3,846,292 | A | 11/1974 | Lecompte, Jr. et al. |
| 3,918,404 | A | 11/1975 | Bunger |
| 3,982,499 | A | 9/1976 | Frankl |

(Continued)

FOREIGN PATENT DOCUMENTS

JP 1998-10225694 8/1998

(Continued)

OTHER PUBLICATIONS

Abstract for JP 1998-10225694 published Aug. 25, 1998.

(Continued)

*Primary Examiner*—Chester T Barry
(74) *Attorney, Agent, or Firm*—Dority & Manning, P.A.

(57) ABSTRACT

The present disclosure is generally directed to a process for decreasing waste material. The process includes loading organic material into a vessel, supplying ozone and water into the vessel, separating the organic material into solid material and liquid material, and reconditioning water from the liquid material for use again. The ozone oxidizes and breaks down at least a portion of the organic material.

16 Claims, 5 Drawing Sheets

U.S. PATENT DOCUMENTS

| | | | | |
|---|---|---|---|---|
| 3,996,105 | A | 12/1976 | Harrison et al. | |
| 4,003,790 | A | 1/1977 | Barnes et al. | |
| 4,042,458 | A | 8/1977 | Harrison et al. | |
| 4,132,637 | A | 1/1979 | Key et al. | |
| 4,178,239 | A | 12/1979 | Lowther | |
| 4,214,887 | A | 7/1980 | van Gelder | |
| 4,256,574 | A | 3/1981 | Bhargava | |
| 4,404,110 | A | 9/1983 | Beazley et al. | |
| 4,451,567 | A | 5/1984 | Ishibashi et al. | |
| 4,608,338 | A | 8/1986 | Hsieh | |
| 4,752,316 | A | 6/1988 | Plovanich et al. | |
| 4,915,842 | A | 4/1990 | Kearney et al. | |
| 5,011,599 | A | 4/1991 | Keatney et al. | |
| 5,070,016 | A | 12/1991 | Hallberg | |
| 5,078,965 | A | 1/1992 | Pearson | |
| 5,342,522 | A | 8/1994 | Marsman et al. | |
| 5,424,195 | A | 6/1995 | Volkwein | |
| 5,447,850 | A | 9/1995 | McCann | |
| 5,472,472 | A * | 12/1995 | Northrop | 71/9 |
| 5,520,888 | A | 5/1996 | Berndt | |
| 5,593,575 | A * | 1/1997 | Cretini | 210/170.06 |
| 5,633,163 | A | 5/1997 | Cameron | |
| 5,641,679 | A | 6/1997 | Pierce | |
| 5,688,685 | A | 11/1997 | Pierce | |
| 5,707,856 | A | 1/1998 | Higa | |
| 5,753,494 | A | 5/1998 | Hater et al. | |
| 5,773,283 | A | 6/1998 | Pierce | |
| 5,854,061 | A | 12/1998 | Horn et al. | |
| 5,897,785 | A | 4/1999 | Billings | |
| 6,056,885 | A | 5/2000 | Wasinger | |
| 6,077,548 | A | 6/2000 | Lasseur et al. | |
| 6,117,324 | A | 9/2000 | Greene et al. | |
| 6,136,194 | A * | 10/2000 | Vogel et al. | 210/605 |
| 6,303,034 | B1 | 10/2001 | Kamiya et al. | |
| 6,340,581 | B1 | 1/2002 | Gaddy | |
| 6,365,048 | B1 * | 4/2002 | Masten et al. | 210/610 |
| 6,375,844 | B1 * | 4/2002 | Ehrlich | 210/605 |
| 6,395,174 | B1 * | 5/2002 | Teran et al. | 210/605 |
| 6,423,229 | B1 | 7/2002 | Mao | |
| 6,500,333 | B1 | 12/2002 | Greene | |
| 6,514,410 | B1 * | 2/2003 | Gantzer | 210/605 |
| 6,555,359 | B2 * | 4/2003 | Cummings | 435/267 |
| 6,558,548 | B2 * | 5/2003 | Svirklys et al. | 210/603 |
| 6,673,241 | B1 * | 1/2004 | Tung et al. | 210/242.1 |
| 6,689,274 | B1 * | 2/2004 | Northrop et al. | 210/601 |
| 6,835,560 | B2 | 12/2004 | Greene | |
| 6,893,565 | B2 | 5/2005 | Greene | |
| 6,982,035 | B1 * | 1/2006 | O'Keefe | 210/258 |
| 2001/0013497 | A1 * | 8/2001 | Kolber | 210/747 |
| 2002/0061270 | A1 | 5/2002 | Osborne | |
| 2002/0192774 | A1 | 12/2002 | Ahring et al. | |
| 2006/0086651 | A1 * | 4/2006 | Sower | 210/173 |

FOREIGN PATENT DOCUMENTS

| | | |
|---|---|---|
| JP | 2000-189103 | 7/2000 |
| JP | 2001-025789 | 1/2001 |

OTHER PUBLICATIONS

Abstract for JP 2000-189103 published Jul. 11, 2000.
Abstract for JP 2001-025789 published Jan. 30, 2001.
Finch, et al., Recovery of a Marker Strain of *Escherichia coli* from Ozonated Water by Membrane Filtration, p. 2894-2896, Dec. 1987, Applied and Environmental Microbiology.
Restaino, et al., Efficacy of Ozonated Water against Various Food-Related Microorganisms, p. 3471-3475, Sep. 1995, Applied and Environmental Microbiology.
Y.H. Chang and B.W. Sheldon, Application of Ozone with Physical Wastewater Treatments to Recondition Poultry Process Waters, p. 1078-1087, Jun. 6, 1988, Journal Series of the North Carolina Agriculture Research Series, Raleigh, NC 27695-.
Finch, et al., Comparison of *Giardia Lamblia* and *Giardia muris* Cyst Inactivation by Ozone, p. 3674-3680, Nov. 1993, Applied and Environmental Microbiology.
Finch, et al., Ozone Inactivation of *Cryptosporidium parvum* in Demand- Free Phosphate Buffer Determined by In Vitro Excystation and Animal Infectivity, p. 4203-4210, Dec. 1993, Applied and Environmental Microbiology.
B.A. Meiners, R.E. Peters and J.B. Mudd, Effects of Ozone on Indole Compounds and Rat Lung Monoamine Oxidase, p. 99-112, 1977, Environmental Research.
Duane L. Peavy and Edward J. Fairchild II, Toxicologic Interactions between Ozone and Bacterial Exdotoxin, p. 63-71, 1987, Environmental Research.
I.Arana, P.Santorum, A.Muela and I.Barcina, Chlorination and ozonation of waste-water:comparative analysis of efficacy through the effect on *Escherichia coil* membranes, p. 883-888, 1999, Journal of Applied Microbiology.
E. Smet & H. Van Langenhove, Abatement of volatile organic sulfur compounds in odorous emissions from bio-industry, Biodegration 9:273-284,1998.
William A. Feder, Bioassaying for Ozone With Pollen Systems, vol. 37:117-123, Jan. 1981, Environmental Health Prospectives.
Serge Chiron, Antonio Rodriguez and Amadeo Fernandez-Alba, Application of gas and liquid chromatography-mass spectrometry to the evaluation of pirimiphos methyl degradation products in industrial water under ozone treatment, Journal of Chromatography A, 823:97-107, 1998.
I.R. Komanapalli and B.H.S. Lau, Inactivation of bacteriophage A, *Escherichia coli*, and *Candida albicans* by ozone, Appl Microbiol Biotechnol, 49:766-769, 1998.
Muela, et al., Discharge of disinfected wastewater in recipient aquatic systems: fate of allochthonous bacterial and autochthonous protozoa populations, Journal of Applied Microbiology, 85:263-270, 1998.
Byun, et al., Gamma Irradiation and Ozone Treatment for Inactivation of *Escherichia coli* O157:H7 in Culture Media, Journal of Food Protection, 61:728-730, 1998.
McKenzie, et al., Aflatoxicosis in Turkey Poults is Prevented by Treatment of Naturally Contaminated Corn with Ozone Generated by Electrolysis, Environment and Health, 1094-1102, 1998.
Klare, et al., Degradation of Nitrogen Containing Organic Compounds by Combined Photocatalysis and Ozonation, Chemosphere, 38:2013-2027, 1999.
Yu, et al., Pretreatment and Biodegradability Enhancement of DSD Acid Manufacturing Wastewater, Chemosphere, 37:487-494, 1998.
Watkins, et al., Ozonation of Swine Manure Wastes to Control Odors And Reduce the Concentrations of Pathogens And Toxic Fermentation Metabolites, Ozone Science & Engineering, 19:425-437, 1997.
Evan, III., Environmental Protection Agency, Cincinnati, Ohio, editor: Ozone In Water And Wastewater Treatment, Ann Arbor Science Publishers, Inc., Ann Arbor, Michigan; Copyright 1972.

* cited by examiner

PROCESS FOR REDUCING WASTE VOLUME

CROSS REFERENCE TO RELATED APPLICATIONS

The present application is based on and claims priority to U.S. Provisional Application Ser. No. 60/753,509 having a filing date of Dec. 23, 2005.

BACKGROUND

Virtually all types of human activities generate various types of organic materials, waste materials, and by-product materials. Organic materials include any substance with molecular moieties containing carbon. Waste has varied forms and characteristics. In terms of the regulation of waste disposal pursuant to federal statutes, rules and regulations, many waste materials are characterized as municipal solid waste pursuant to 42 USC 691 et seq. Other categories of waste materials include animal waste either as it exists in confined animal production facilities or as it may be found in confinement ponds or lagoons. Other wastes from specific industries that may, but are not necessarily included as municipal solid waste, include materials produced during food processing and rendering, wood and timber processing, and chemical and petroleum manufacturing and processing.

Municipal solid waste, more commonly known as trash or garbage, includes everyday items such as paper, food scraps and yard trimmings that are disposed of and may ultimately end up at landfills. According to the United States Environmental Protection Agency, in 2001 U.S. residents, businesses, and institutions produced more than 229 million tons of municipal solid waste, which amounts to approximately 4.4 pounds of waste per person per day, up from 2.7 pounds per person per day in 1960. Although source reduction, reuse, recycling, and composting can divert portions of municipal solid waste from disposal, a large amount of waste must still be placed in landfills.

Modern landfills are expensive facilities that require a great deal of funding to build and maintain. Landfills are built in suitable geological areas away from faults, wetlands, flood plains, or other restricted areas. Typically, liners formed from geomembrane or plastic sheets reinforced with two feet of clay on the bottom and sides of landfills are installed. In addition, general maintenance including insect and rodent control and ground water monitoring add to landfill costs. Also, closure and postclosure care, which includes covering landfills and providing long-term care of closed landfills, can further add to costs.

A need currently exists for an improved process for reducing organic material, organic waste, and landfill mass. In particular, a need exists for a process that can reduce the volume of municipal waste. Additionally, a system for converting one organic moiety to another would allow wide and varied products which may be economically valuable.

SUMMARY

Objects and advantages of the disclosure will be set forth in part in the following description, or may be obvious from the description, or may be learned through the practice of the disclosure.

The present disclosure is generally directed to a process for decreasing waste material. The process includes loading organic material into a vessel, supplying ozone and water into the vessel, separating the organic material into solid material and liquid material, and reconditioning water from the liquid material for use again. The ozone oxidizes and breaks down at least a portion of the organic material.

In certain embodiments, organisms may be added to the organic material after supplying ozone and water into the vessel. One or more products that are generated by the organisms may be collected. Organisms may be added to the solid material or the liquid material. Again, one or more products that are generated by the organisms may be collected. The organic material may be reduced so as to create more surface area on the organic material to facilitate oxidizing and breaking down at least a portion of the organic material. The vessel may include nozzles, the nozzles projecting liquid or air into the vessel such that the 10 size of the organic material is reduced so as to create more surface area on the organic material to facilitate oxidizing and breaking down at least a portion of the organic material. A portion of the organic material may be separated with a macerator in combination with a centrifuge. A portion of the organic material may be separated with a centrifuge.

In another exemplary embodiment, a process for decreasing waste material is disclosed. The process includes loading organic material into a first vessel, supplying ozone and water into the first vessel, separating the organic material into solid material and liquid material, and reconditioning water from the liquid material for use again. The ozone oxidizes and breaks down at least a portion of the organic material and excess liquid material overflows into a second vessel.

Other features and aspects of the present disclosure are discussed in greater detail below.

BRIEF DESCRIPTION OF THE DRAWINGS

A full and enabling disclosure of the present disclosure, including the best mode thereof to one of ordinary skill in the art, is set forth more particularly in the remainder of the specification, including reference to the accompanying figures in which.

Figure 1:
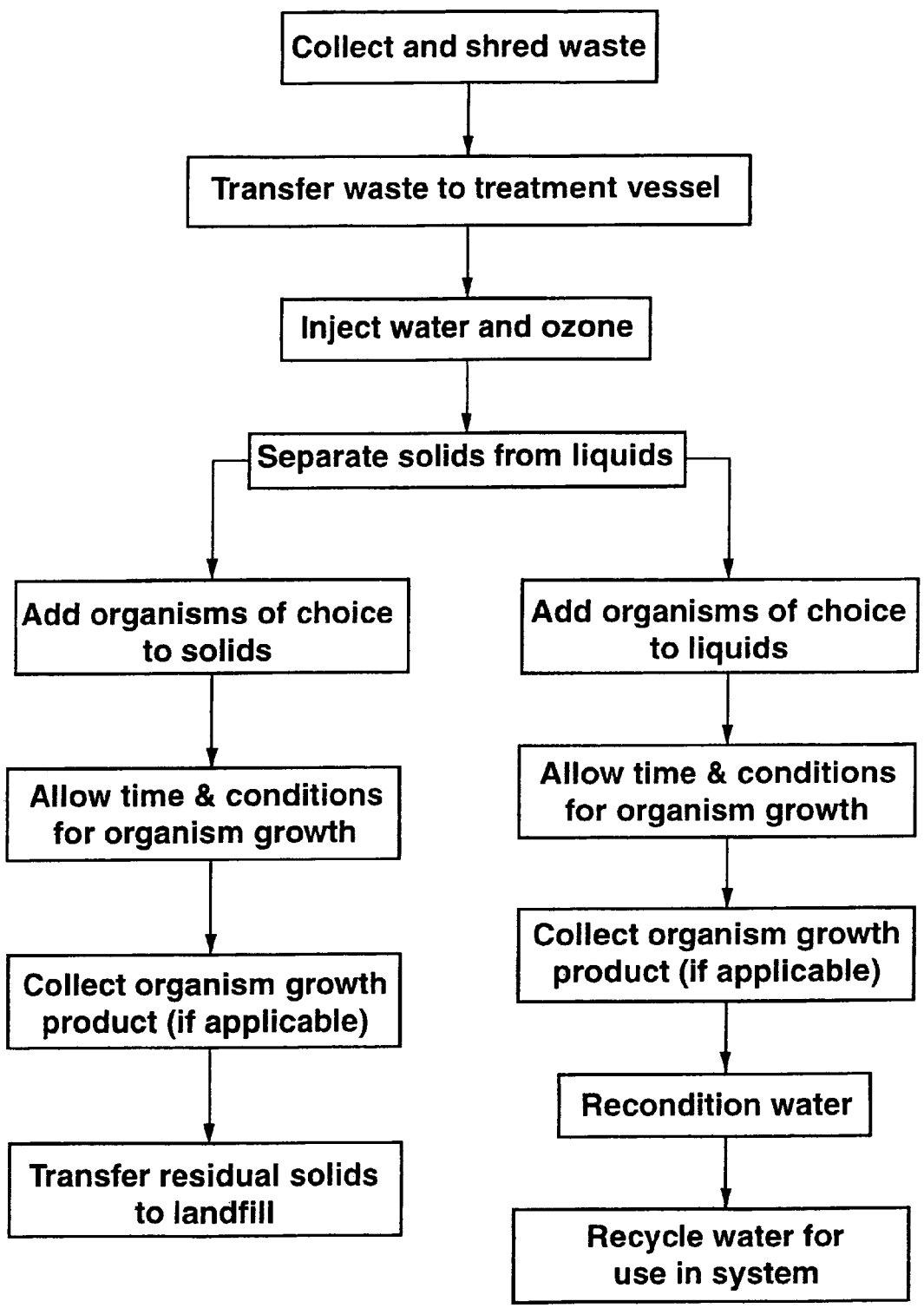
FIG. 1 is a flow chart of an embodiment of a process for reducing waste materials.

Repeat use of reference characters in the present specification and drawings is intended to represent same or analogous features or elements of the present disclosure.

DETAILED DESCRIPTION

Reference now will be made in detail to the embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure cover such modifications and variations and their equivalents.

The inventor of the present invention has provided improvements and advancements in systems and processes for reducing waste volume as disclosed in U.S. Pat. No. 6,893,565, which is incorporated herein by reference in its entirety.

In the above patent, organic material is mixed with water and ozone and combined with organisms for reduction of waste. In one embodiment, the present disclosure relates to further improvements in systems and processes for reducing waste volume. Waste material is mixed with water and ozone and combined with organisms for reduction of waste. In another embodiment, waste materials are treated with ozone with added water, if necessary, to result in a reduction in waste volume. In another embodiment, the present disclosure is generally directed to a system and process for converting organic moieties into chemically different organic moieties. If organic materials contain sufficient water for allowing oxidation of at least some of the organic materials upon ozonation, additional water does not need to be added.

As used herein, "waste" refers to any substance that is no longer desired in its present state or location. Organic materials include any substance with molecular moieties containing carbon. "Organism" refers to any prokaryotic or eukaryotic organism including macro- and microorganisms and tissue culture. An organism used in the present disclosure can be a plant, a protista such as bacteria, a monera, a fungus, or other prokaryotic or eukaryotic entities. The present disclosure also encompasses the use of genetically engineered organisms and microorganisms. The organisms carry out growth and metabolism thereby yielding a cellular product. As used herein, a cellular product refers to any intracellular or extracellular product produced by any respirative (aerobic or anaerobic), fermentative, photosynthetic or any similar growth process. In general, fermentation can be defined as an ATP-generating metabolic process in which organic compounds serve both as electron donors (becoming oxidized) and electron acceptors (becoming reduced). Respiration is an ATP-generating metabolic process in which either organic or inorganic compounds serve as electron donors (becoming oxidized) and inorganic compounds serve as the ultimate acceptors (becoming reduced). Photosynthesis refers to the conversion of energy from light to chemicals.

One embodiment of a general flow diagram of the process of the present disclosure for reducing waste materials is illustrated in FIG. 1. Waste material is collected and shredded. Waste material is transferred to a treatment vessel and injected with water and ozone. The solid material is separated from the liquid material and organisms are added to each. Conditions are made favorable for organism growth in both the solid and liquid material. If applicable, organism growth product is collected. Residual solids are transferred to a landfill while water is reconditioned from the residual liquid and recycled for use again.

Figure 2:
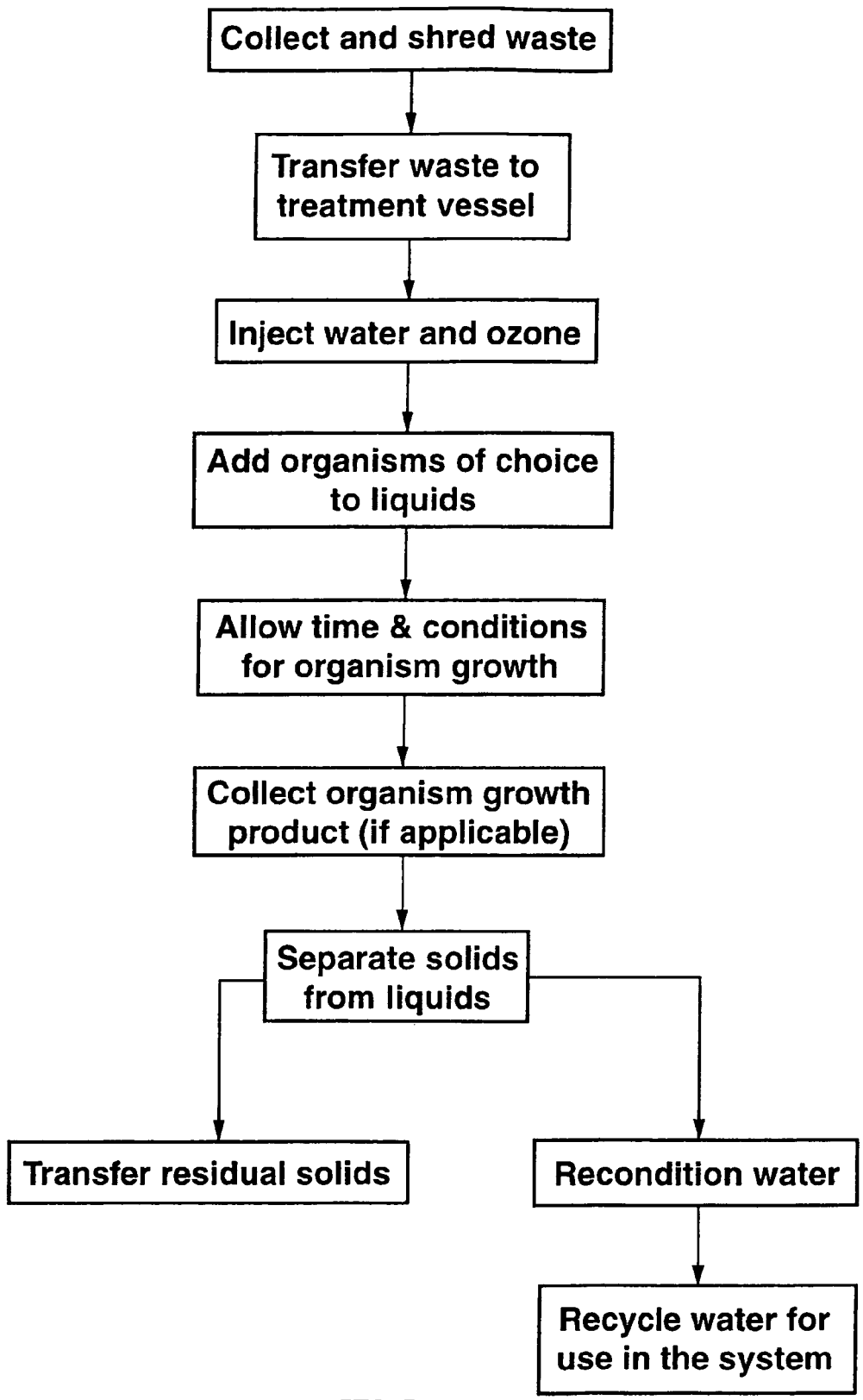
FIG. 2 is a flow chart of an embodiment of a process for reducing waste materials.

Referring to FIG. 2, another embodiment of a general flow diagram of the process of the present disclosure for converting waste materials is illustrated. Waste material is collected and shredded. Waste material is transferred to a treatment vessel and injected with water and ozone. In this embodiment, as opposed to the process illustrated in FIG. 1, the material containing solid and liquid is not separated prior to the addition of organisms. Thus, organisms are added to the solid and liquid slurry and conditions are made favorable for organism growth. If applicable, organism growth product is collected. The solid material is then separated from the liquid material and residual solids are transferred to a landfill while water is reconditioned from the residual liquid and recycled for use again.

Figure 3:
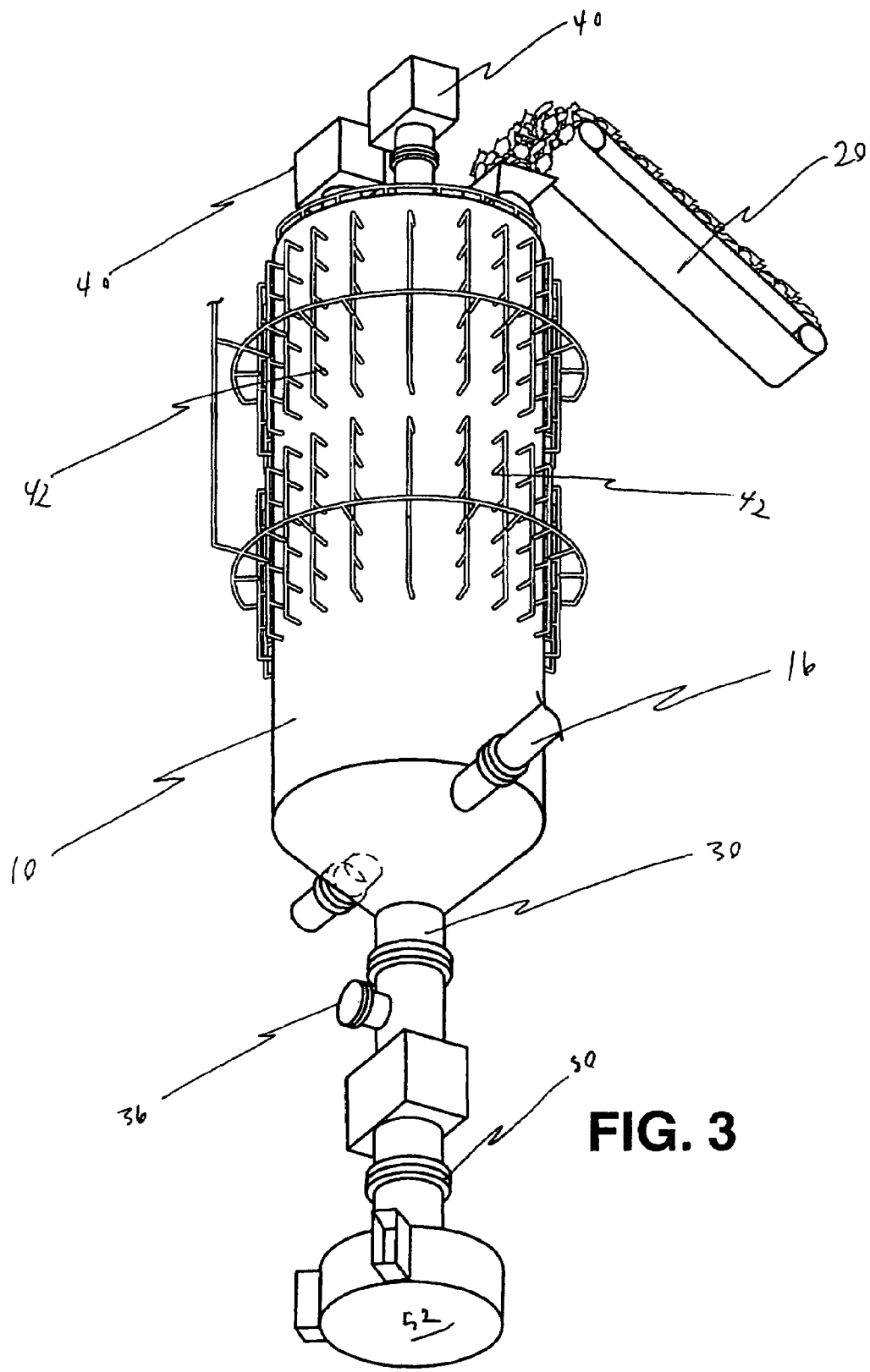
FIG. 3 depicts an embodiment of a process for reducing waste materials.

With reference to FIG. 3, an embodiment of a system for reducing a volume of waste is illustrated. The system includes a vessel 10 for receiving waste. The vessel 10 has a sealable opening for receiving waste. The vessel 10 is generally cylindrical and made from stainless steel or any other suitable material as would be known in the art earthen vessel or a concrete vessel. The diameter and height of the vessel 10 can vary depending on the amount of material being processed. The vessel 10 empties into discharge element 30 which includes a clean-out/access port 36 to allow debris blocking the discharge element 30 to be removed.

Figure 4:
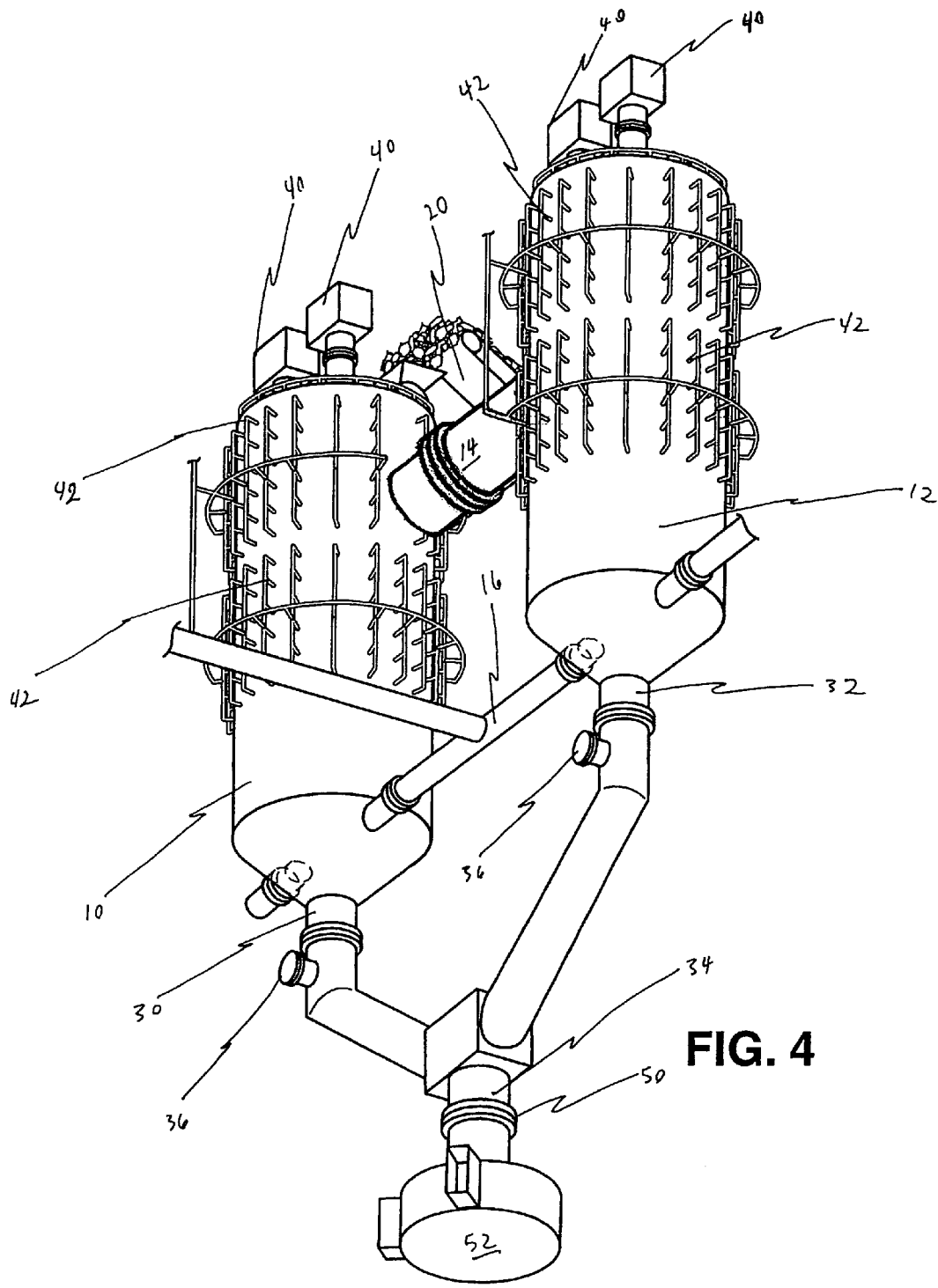
FIG. 4 depicts an alternative embodiment of a process for reducing waste materials.

In some embodiments, as illustrated in FIG. 4, the system includes two vessels comprising a primary vessel 10 and an overflow vessel 12. Each of the vessels 10, 12 are similar to the vessel 10 described in FIG. 3. The utilization of two or more vessels permits overflow liquid to pass from the primary vessel 10 to the overflow vessel 12 allowing more material to be processed. The overflow tube is sized to allow unimpeded flow across to the adjoining tank(s).

It should be understood that the primary vessel 10 may act as the overflow vessel 12 whereby waste can be added to the overflow vessel 12 once processing of waste in the primary vessel 10 nears completion. Such embodiments may include loading mechanisms on both vessels so as to limit equipment wear and tear between the two tanks and also to assist in cleaning the system periodically.

The vessels 10, 12 are generally cylindrical and are arranged side by side with one another. The vessels 10, 12 are connected at their top portions by an overflow tube 14. The inside of the vessels 10, 12 may include a screen to prevent solid waste material from passing through the overflow tube 14. The vessels 10, 12 each empty into discharge elements 30, 32 which join together to form one discharge pipe 34. A clean-out/access port 36 is mounted on one or both of the discharge elements 30, 32 to allow debris blocking the discharge elements 30, 32 to be removed.

Figure 5:
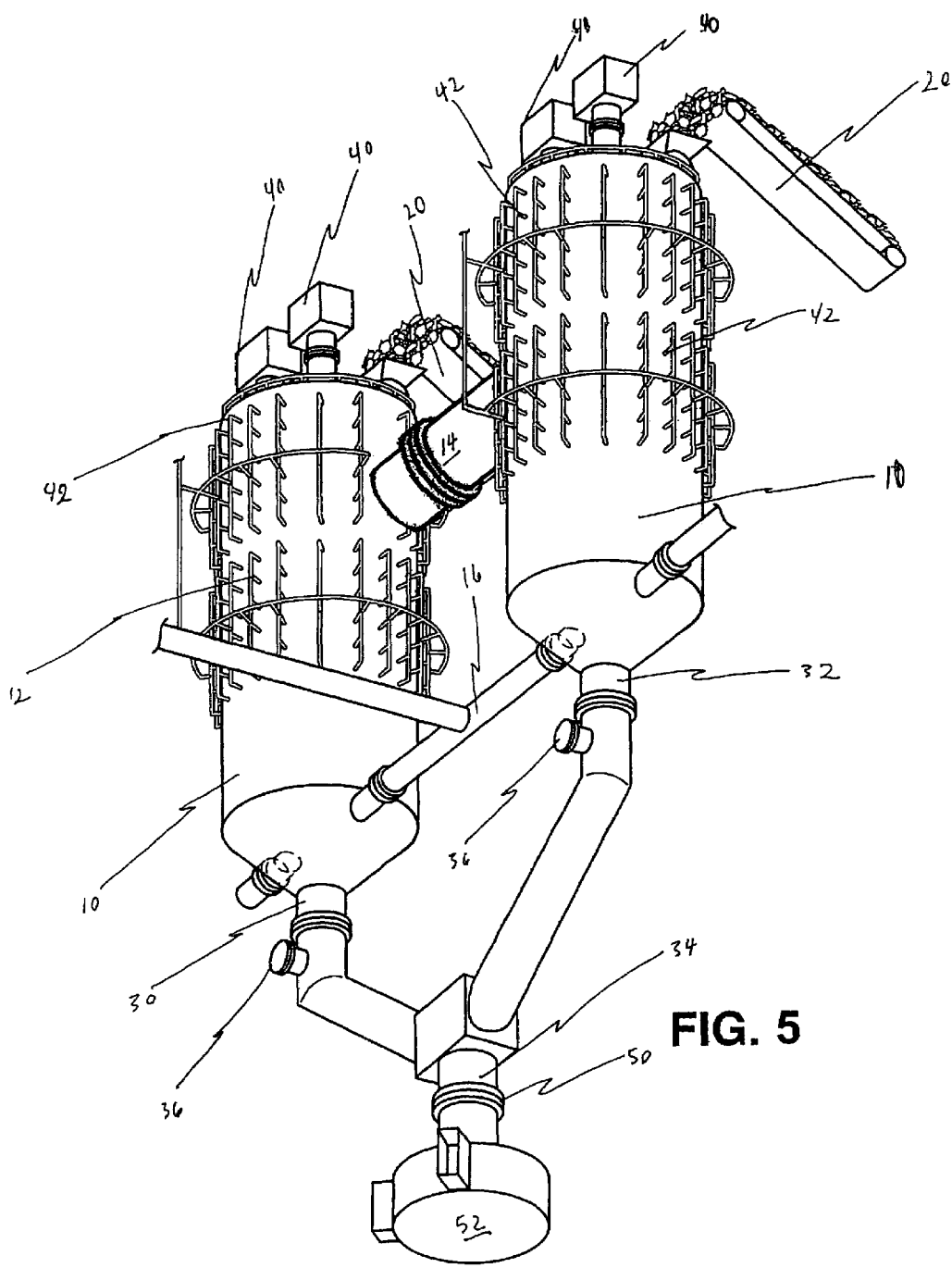
FIG. 5 depicts an alternative embodiment of a process for reducing waste materials.

In some embodiments, as illustrated in FIG. 5, the system includes two vessels comprising primary vessels 10. In other embodiments, more than two vessels may be utilized.

In some embodiments, the treatment vessel can be sized to a particular location. Large scale treatment vessels could be used on industrial scale whereas smaller units could be used as necessary in restaurants, dining halls, homes, ships, sporting and entertainment events, campgrounds, etc. The treatment system also can be a stationary system or a mobile system. In addition, it should be understood that such a treatment vessel may be of any size or shape to accommodate the particular materials or application desired and constructed of various materials. In one embodiment, the treatment vessel can be constructed in a manner which allows greatest contact of ozone with organic materials as can be accomplished by any of numerous mechanisms recognized to one of ordinary skill in the art.

As described above and illustrated in FIGS. 3, 4 and 5 waste material is transferred to the vessel(s) and injected with water and ozone. The vessel(s) have pressure equalizer/release valves 40 to allow for excess pressure to be released. The vessel(s) 10, 12 have pressure injection nozzles 42 spaced along the length of the vessel(s).

In some embodiments, the nozzles 42 are spaced so as to cover at least 30% of the length of the vessel(s). In some embodiments, the nozzles 42 to are spaced to cover at least 40% of the length of the vessel(s). In some embodiments, the nozzles 42 to are spaced to cover at least 50% of the length of the vessel(s). In some embodiments, the nozzles 42 to are spaced to cover at least 60% of the length of the vessel(s). In some embodiments, the nozzles 42 to are spaced to cover at least 70% of the length of the vessel(s). In some embodiments, the nozzles 42 to are spaced to cover the entire length of the vessel(s).

In some embodiments, the nozzles 42 can also encircle the vessel(s). In some embodiments, the nozzles are spaced every 30 degrees around the circumference of the vessel(s). In some embodiments, the nozzles are spaced every 60 degrees around the circumference of the vessel(s). In some embodiments, the nozzles are spaced every 90 degrees around the circumference of the vessel(s). In some embodiments, the nozzles are spaced every 120 degrees around the circumference of the vessel(s).

The nozzles 42 generally surround the vessel(s) and aid in reducing the size of material in the vessel. It should be understood that the nozzles 42 can be positioned at any location on vessel(s) to best assist in reducing the size of material within the vessel(s). The nozzles 42 are capable of both high and low pressure. In some embodiments, the nozzles 42 are capable of producing greater than 1750 pounds per square inch (psi) of pressure.

According to the present disclosure, various organic materials are first collected. If desired, the organic materials can be pre-soaked with water or another solvent, pre-treated, pre-heated, pre-sorted or pre-separated prior to contact with ozone. For example, in one embodiment, inorganic materials, such as glass, metal, or the like can first be removed prior to contact with ozone.

The materials can also be sized before or during ozone treatment. For example, the waste materials can be ground, milled or pulverized as desired. Reducing the size of the waste materials will create more surface area to facilitate processing. In some embodiments, other methods of reducing size before or during ozone treatment may be employed. Such methods could include shredding, grinding, chopping, cutting, etc. If desired, the reduction of size can be accomplished within the treatment vessel by use of high pressure water or gas action or by the use of mechanical action.

With reference to FIGS. 3, 4 and 5, the waste is moved into primary vessel 10 and/or overflow vessel 12 on a loading conveyer 20. The waste is emptied into the top portion of the primary vessel 10 and/or overflow vessel 12. In some embodiments, the waste can be added at other sections of the vessel include the bottom or side. In some embodiments, the primary vessel 10 is filled as fully as possible with waste while the overflow vessel 12 is not filled with waste at all or is filled to a lesser degree so as to allow water to overflow into the adjoining vessel.

The waste also can be brought into the vessels by other methods as would be known in the art. Materials can be transported into the treatment vessel in batches or in continuous feed systems. In batches, the materials may be added via a bucket, a scoop, a rail car or any of numerous other methods as would be known in the art. In continuous feed mechanisms, materials may be transported to the treatment vessel by conveyor, auger, compressed air movement, hydraulic press, or any of numerous other methods as would be known in the art. If desired, materials may be transferred into the treatment vessel in the form of a slurry or a solution. Additionally, the treatment tanks may be placed in an area such that trucks or other mechanical or labor powered devices could dump materials directly into the top of the treatment vessel.

Once the waste materials have been selected and collected, the materials are contacted with water and ozone. With reference to FIGS. 3, 4 and 5, the nozzles 42 shred the waste located in the primary vessel 10 and/or overflow vessel 12 with high pressure and low pressure water and/or gas. The streams of water and/or gas also may be pulsed and/or staggered to assist in further breaking up the materials.

Depending on the nature of the organic materials to be treated, the process conducted within the treatment vessel could be ozonating the materials or adding water and ozonating the materials or actively agitating and disrupting particles through mechanical action while ozonating. The agitating and mechanical disruptive action can be accomplished by any of numerous mechanisms or physical actions that are recognized to one of ordinary skill in the art including but not limited to augers, agitators, rotating vessels, knives, different pressures of water injection, different pressures of compressed gas injection (which could also serve to allow pH adjustment—for instance inject ammonia), choppers, blades, paddles, grinders, shredders, compacters, pounding devices, pumps, etc. or any combination thereof.

The primary vessel 10 and/or overflow vessel 12 may develop foam and, in some embodiments, an antifoam agent is utilized to dissipate such foam.

Ozone can oxidize waste materials into a substrate that can sustain biological metabolic processes such as fermentation, respiration or photosynthesis. In particular, once contacted with ozone, the organic compounds are converted into substrates such as saccharides (sugars) that can be used as a growth medium for organisms. Alternatively, the oxidized waste can be contacted with a selected enzyme for conversion into a useful product. This process degrades the organic compounds contained in the materials into smaller organic compounds.

Many different methods can be used in order to contact the waste materials with ozone for decomposing the organic compounds. For example, as illustrated in FIGS. 3, 4 and 5, in one embodiment, the waste materials can be contained within a vessel and ozone can be fed utilizing an ozonator 16 toward the bottom of the vessel and bubbled through the mixture. Typically, the waste may be contacted with ozone once the primary vessel 10 is at least one third full of water depending on the nature of the material in the treatment vessel. In another embodiment, ozone also can be introduced to the vessel via ozone-saturated water through the injectors. In yet another embodiment, the treatment vessel can be a continuous treatment system with organic materials, water and ozone in continuous contact in a flow through system.

In still a further embodiment of the present disclosure, ozonation of the waste materials can be carried out in a pressurized vessel. In this embodiment, a mixture or an aqueous solution containing the organic compounds can be placed in a vessel under pressure. Ozone can then be introduced into the chamber for breaking down the organic compounds.

The amount of ozone contacted with the waste materials will depend upon the particular application and the type of materials being treated. In general, the concentration of ozone contacting the waste materials should be at least 0.01 ppm. Preferably, however, greater concentrations of ozone are used during the process. For instance, for most applications, ozone should be fed at a concentration sufficient to saturate or to nearly saturate the mixture/solution with ozone.

Other chemical moieties can be added to the mixture/solution before, during or after ozonation. In one embodiment, hydrogen 1o peroxide may be added to enhance ozonation. In another embodiment, pH adjustment can be performed before, during or after ozonation.

The amount of ozone that it takes to saturate an aqueous solution depends upon the temperature, pressure and nature of the solution. In general, greater amounts of ozone can be dissolved into the solution at lower temperatures. Thus, in one embodiment, the aqueous solution being treated in accordance with the present disclosure can be cooled prior to or during ozonation. For instance, in one embodiment, the temperature of the aqueous solution can be maintained below about 20° C., and particularly below about 15° C. The solubility of ozone in water at 20° C. is about 575 milligrams per liter, while the solubility of ozone in water at 10° C. is about 785 milligrams per liter. In another embodiment, the mixture/slurry of materials can be cooled to enhance ozone solution followed by an increase in temperature to force free radical oxygen release from ozone.

Similar to the concentration of ozone, the amount of time the waste materials are contacted with ozone also depends upon the particular application. For most applications, however, ozonation should continue until a portion of the organic compounds are broken down into smaller hydrocarbon species capable of being used in cellular processes.

During ozonation, the pH of the aqueous solution may have a tendency to alternatively decrease and increase with a gradual overall downward trend. Should the pH of the solution vary too greatly from neutral (generally between a pH of 5 and 9), subsequent cellular growth may be adversely affected depending on the organism cultured. Consequently, in some applications, a base or an acid can be added to the aqueous solution prior to or during or after ozonation to adjust pH to the optimum pH range for the microbial population. During ozonation of materials and particularly of protein moieties, significant foaming can occur. Antifoam agents and physical processes designed to reduce/prevent foaming as apparent to those skilled in the art may be employed to reduce foaming, if necessary.

Prior to or after ozonation, various enzymes can also be added to the aqueous solution to assist in breaking down the waste materials. For instance, if the waste materials contain cellulosic materials, cellulase enzyme can be added to the materials. The enzyme will break down cellulose increasing the availability of organic compounds that may be released during the process of the present disclosure. Other enzymes that can be added include lipases, proteases, amylases, and the like.

Once the aqueous solution containing the waste materials has been ozonated, the remaining solid materials can be separated, if desired, from the aqueous solution by a variety of means including but not limited to settling, centrifugation, and filtering. Separating the materials, however, can occur prior to ozonation or after contact with organisms.

As described previously, the vessels 10, 12 each empty into discharge elements 30, 32 which join together to form one discharge pipe 34. A clean-out/access port 36 is mounted on one or both of the discharge elements 30, 32 to allow debris blocking the discharge elements 30, 32 to be removed.

In some embodiments, once the mixture of waste materials has been ozonated, a slurry is produced containing a growth medium (substrate) for organisms. The substrate can contain, for instance, sugars, proteins, lipids, inorganic compounds, minerals, vitamins, and other nutrients. In accordance with the present disclosure, the oxidized medium may be contacted with organisms and/or enzymes for carrying out the processes of growth, metabolism and bioconversion via fermentative, respirative, photosynthetic, or similar pathways. Particular organisms can be selected for producing cells or specific end products that can be collected and used as desired.

In some embodiments, organisms consume the oxidized waste material which results in an eventual reduction of volume of the solid waste. Suitable organisms may be selected as would be known to one of ordinary skill in the art. It may be useful to heat the waste or organic materials during or after ozonating to force free radical oxygen to be released from ozone, thereby forcing an oxidation reaction.

Once organisms are added to the ozonated slurry, the organisms are allowed to grow to result in reduction of waste volume. In such an embodiment, a product would not necessarily have to be collected—loss of product to the atmosphere as gas or small particulate may be the desired result (i.e.—the "useful product" is a reduction in volume of the material). The reduction in volume of the waste is at least 1% by volume. However, the reduction of volume may be greater or less than this amount depending on the particular conditions present.

In some embodiments, the organism growth phase could occur within the treatment vessel. In this embodiment, materials would be mixed with water, if necessary, and ozonated. Upon reaching a degree of oxidation to be determined for each particular material, ozonation would be terminated. Subsequently, organisms could be added to the resultant substrate within the treatment vessel. Temperature and pH adjustments could be performed, if necessary. Ion removal could be performed, if necessary.

In some embodiments, microorganisms can be selected that will convert the fermentable compounds contained within the slurry into ethanol. The ethanol can then be collected and separated from the slurry and used, for instance, as an energy source.

In still another embodiment of the present disclosure, the oxidized waste materials can be fed to an organism for the production of hydrocarbons, such as methane gas. As the methane gas is produced, the gas can be collected and used as a fuel source.

In another embodiment, the ozonated materials can be exposed to an organism growth phase followed by a repeated ozonation phase followed by another organism growth phase. This cycle could be repeated as many times as desired. In yet another embodiment, materials that have been ozonated and exposed to an organism growth phase could be mixed in with untreated materials for a repeat ozonation/organism growth phase cycle.

The manner in which the organisms are supplied with the oxidized medium can also vary. For instance, in one embodiment, a batch system can used in which the aqueous medium is placed into a reservoir containing the organisms. The aqueous substrate can remain in contact with the organisms until microbial growth and metabolism has reached the desired endpoint.

In still another embodiment, the organisms can be contained in an aqueous culture that continuously contacts the ozonated solution in a continuous culture, chemostat-type process. For example, in this embodiment, the ozonated solution can be fed into a chemostat chamber which contains a solution comprising organisms. Fermentation and other growth processes can occur within the chemostat chamber as the organisms conduct metabolism. Excess solution containing the desired organism and/or product can be collected. In another example, organisms can be bound in a type of stationary phase and the ozonated solution can be fed through the organisms.

In some embodiments, microorganisms can be supplied to consume the organic materials. Such microorganisms include but are not limited to *Ruminococcus, Cellulomonas, Pseudomonas, Acetobacter, Lactobacillus, Lactococcus*, and *Alcaligenes*. Suitable microorganisms may include fungi or bacteria and particularly aerobic microorganisms. Anaerobic microorganisms would be utilized for methane generation. Prokaryotic or eukaryotic organisms may be used. One or more species of microorganisms can be supplied with the result being a reduction in waste.

In some embodiments, air may be added to promote the growth of aerobic microorganisms and to help speed the degradation of the waste. However, in conditions favorable to growth, temperatures may increase quickly as a result of the rapid proliferation of microorganisms. In some embodiments, the heat produced from the rapid proliferation of microorganisms may be recaptured. Such a method of recapturing heat may include utilizing tubes or pipes to redirect heat away from the rapid proliferation of microorganisms. In another embodiment, generated heat could be redirected to the treatment vessel to maintain or raise the temperature to enhance the release of free radical oxygen from the ozone moiety.

In certain embodiments, a temperature sensor may be utilized to detect such rapid changes in temperature. If needed, various methods may be utilized to slow growth of the microorganisms and decrease the temperature of the waste. One such method that may be utilized with aerobic microorganisms involves adding a gas, which will create anaerobic conditions. Gases such as carbon dioxide or nitrogen would be suitable to create anaerobic conditions. Another such method would be to allow aerobic organisms to consume the available oxygen thus rendering the residual materials anaerobic.

In some embodiments, the process could conclude after ozonation of the materials without subsequent organism growth. Additionally, organism growth could be delayed until a later time or place.

As illustrated in FIG. 1, in some embodiments, the liquid and solid waste slurry are separated prior to the addition of organisms. As illustrated in FIGS. 3, 4 and 5, the discharge pipe 34 empties into a macerator 50 in connection with a centrifuge 52 which may be utilized to further break down and separate the waste. Organisms may be added to both the liquid waste as well as the solid waste resulting in reduction of waste and/or generation of a useful product from each. Once separated, the liquid waste may be treated so as to recondition and recycle water for use in the vessels again. The reconditioning process removes contaminants from the water for reuse in the vessel. The solids may pass through an aerobic solids digester to a landfill. Each material may pass through additional treatment before being sent to a landfill. In some embodiments, the ozonated solids may be composted.

In yet another embodiment, alternative solids/liquid separation devices/methods could be utilized in place of the macerator and centrifuge. Such solids/liquids separation devices/methods could include presses, gravity settling basins, etc. Additionally, in other embodiments, a centrifuge may be used without an associated macerator.

These and other modifications and variations to the present disclosure may be practiced by those of ordinary skill in the art, without departing from the spirit and scope of the present disclosure, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the disclosure so further described in such appended claims.

What is claimed is:

1. A process for decreasing waste material comprising:
   loading organic material into a vessel, said vessel having a sealable opening for receiving said organic material;
   supplying ozone and water into said vessel, said ozone oxidizing and breaking down at least a portion of said organic material;
   adding organisms to said organic material;
   collecting one or more products generated by said organisms;
   separating said organic material into solid material and liquid material; and
   reconditioning water from said liquid material; and
   recycling the water for use again in the process.

2. The process of claim 1, further comprising the step of adding organisms to said solid material or said liquid material.

3. The process of claim 2, further comprising the step of collecting one or more products generated by said organisms added to said solid or said liquid material.

4. The process of claim 1, further comprising the step of reducing the size of said organic material so as to create more surface area on said organic material to facilitate oxidizing and breaking down at least a portion of said organic material.

5. The process of claim 1, wherein said vessel includes nozzles, said nozzles projecting liquid or air into said vessel such that the size of said organic material is reduced so as to create more surface area on said organic material to facilitate oxidizing and breaking down at least a portion of said organic material.

6. The process of claim 1, wherein at least a portion of said organic material is separated with a macerator in combination with a centrifuge.

7. The process of claim 1, wherein at least a portion of said organic material is separated with a centrifuge.

8. A process for decreasing waste material comprising:
   loading organic material into a first vessel, said vessel having a sealable opening for receiving said organic material;
   supplying ozone and water into said first vessel, said ozone oxidizing and breaking down at least a portion of said organic material and wherein excess liquid material overflows into a second vessel;
   adding organisms to said organic material;
   collecting one or more products generated by said organisms;
   separating said organic material into solid material and liquid material; and
   reconditioning water from said liquid material; and
   recycling the water for use again in the process.

9. The process of claim 8, further comprising the step of adding organisms to said solid material or said liquid material.

10. The process of claim 9, further comprising the step of collecting one or more products generated by said organisms added to said solid material or said liquid material.

11. The process of claim 8, further comprising the step of reducing the size of said organic material so as to create more surface area on said organic material to facilitate oxidizing and breaking down at least a portion of said organic material.

12. The process of claim 8, wherein said vessel includes nozzles, said nozzles projecting liquid or air into said vessel such that the size of said organic material is reduced so as to create more surface area on said organic material to facilitate oxidizing and breaking down at least a portion of said organic material.

13. The process of claim 8, wherein at least a portion of said organic material is separated with a macerator in combination with a centrifuge.

14. The process of claim 8, wherein at least a portion of said organic material is separated with a centrifuge.

15. The process of claim 8, further comprising:
   loading additional organic material into said second vessel;
   supplying ozone and water into said second vessel, said ozone oxidizing and breaking down at least a portion of said additional organic material and wherein excess liquid material overflows into said first vessel;

separating said additional organic material into solid material and liquid material; and reconditioning water from said liquid material for use again.

16. The process of claim 15, further comprising the step of adding organisms to said organic material after supplying ozone and water into said vessel.

* * * * *